US008142446B2

(12) United States Patent
Shan

(10) Patent No.: US 8,142,446 B2
(45) Date of Patent: Mar. 27, 2012

(54) TOOLKIT FOR IMPLANTING AN INTRACORPOREAL LEAD SUCH AS FOR CARDIAC PACING OR SENSING

(75) Inventor: Nicolas Shan, Vincennes (FR)

(73) Assignee: Sorin CRM S.A.S., Clamart Cedex (FR)

( * ) Notice: Subject to any disclaimer, the term of this patent is extended or adjusted under 35 U.S.C. 154(b) by 635 days.

(21) Appl. No.: 12/212,429

(22) Filed: Sep. 17, 2008

(65) Prior Publication Data

US 2009/0076522 A1 Mar. 19, 2009

(30) Foreign Application Priority Data

Sep. 18, 2007 (FR) ...................................... 07 06551

(51) Int. Cl.
*A61B 19/00* (2006.01)
(52) U.S. Cl. .................................... 606/129; 604/167.01
(58) Field of Classification Search .................. 606/129; 604/160, 523, 167.03, 161, 164.05, 167.01–167.06; 607/122

See application file for complete search history.

(56) References Cited

U.S. PATENT DOCUMENTS

| 4,512,766 | A | | 4/1985 | Vailancourt | |
|---|---|---|---|---|---|
| 5,098,393 | A | * | 3/1992 | Amplatz et al. | 604/167.03 |
| 5,125,904 | A | * | 6/1992 | Lee | 604/256 |
| 5,312,355 | A | * | 5/1994 | Lee | 604/160 |
| 6,159,198 | A | | 12/2000 | Gardeski et al. | |
| 6,625,496 | B1 | | 9/2003 | Ollivier | |
| 6,966,896 | B2 | * | 11/2005 | Kurth et al. | 604/167.06 |
| 7,335,182 | B1 | * | 2/2008 | Hilaire | 604/27 |
| 2004/0176781 | A1 | | 9/2004 | Lindstrom et al. | |
| 2005/0010238 | A1 | | 1/2005 | Potter et al. | |
| 2005/0228346 | A1 | * | 10/2005 | Goode et al. | 604/164.07 |
| 2007/0123825 | A1 | | 5/2007 | King et al. | |

FOREIGN PATENT DOCUMENTS

| EP | 1002553 | 5/2000 |
|---|---|---|
| EP | 1155710 | 11/2001 |

* cited by examiner

*Primary Examiner* — Gary Jackson
*Assistant Examiner* — Katrina Stransky
(74) *Attorney, Agent, or Firm* — Orrick Herrington & Sutcliffe, LLP

(57) ABSTRACT

A toolkit for implanting an intracorporal lead, preferably a cardiac sensing/pacing lead. This toolkit includes a guide-catheter (10), having a sheath (12) with an internal lumen (42) opened at its distal and proximal ends, and cuttable along a generatrix in order to allow extracting of the guide-catheter after use. A hemostatic valve (14) is mounted at the proximal end (40) of the guide-catheter, for selectively filling, or not, the internal lumen of the guide-catheter at its input end. The valve is frangible in at least two parts, each dissociable from the guide-catheter at both sides around a median axial plane. The valve comprising a mobile element sliding on the guide-catheter between two extreme positions, with an opened position where the proximal end (40) of the guide-catheter (10) freely emerges out of the valve so as to allow access to said internal lumen, and a closed position where this proximal end of the guide-catheter is filled in a tight manner.

11 Claims, 4 Drawing Sheets

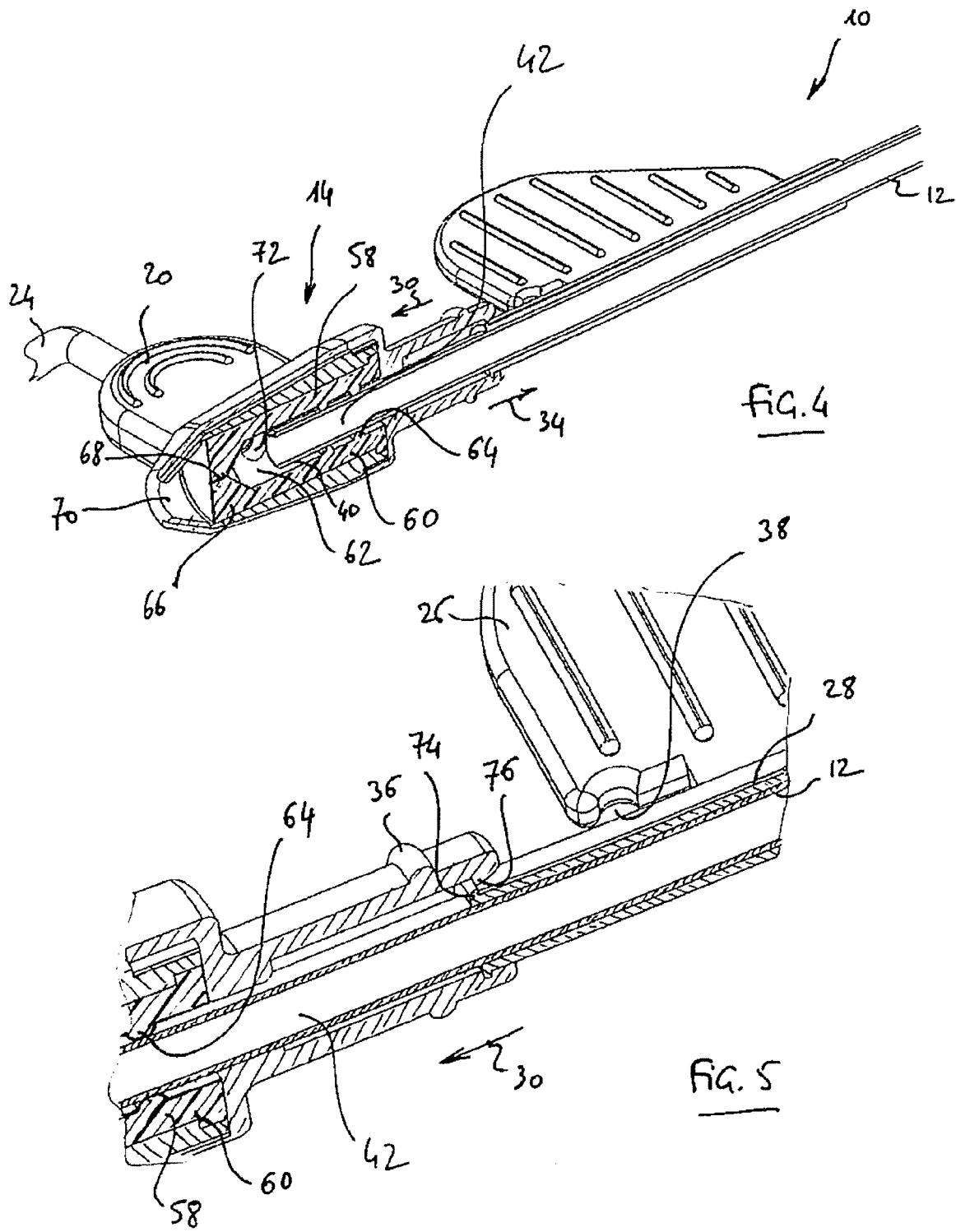

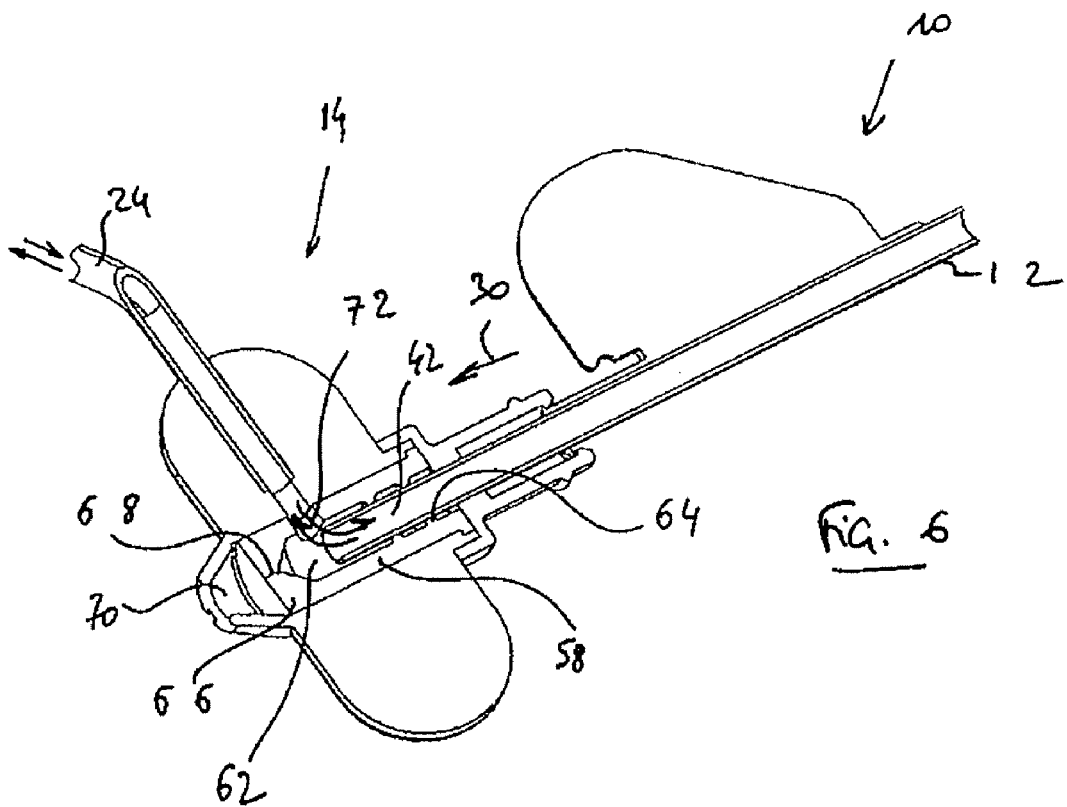
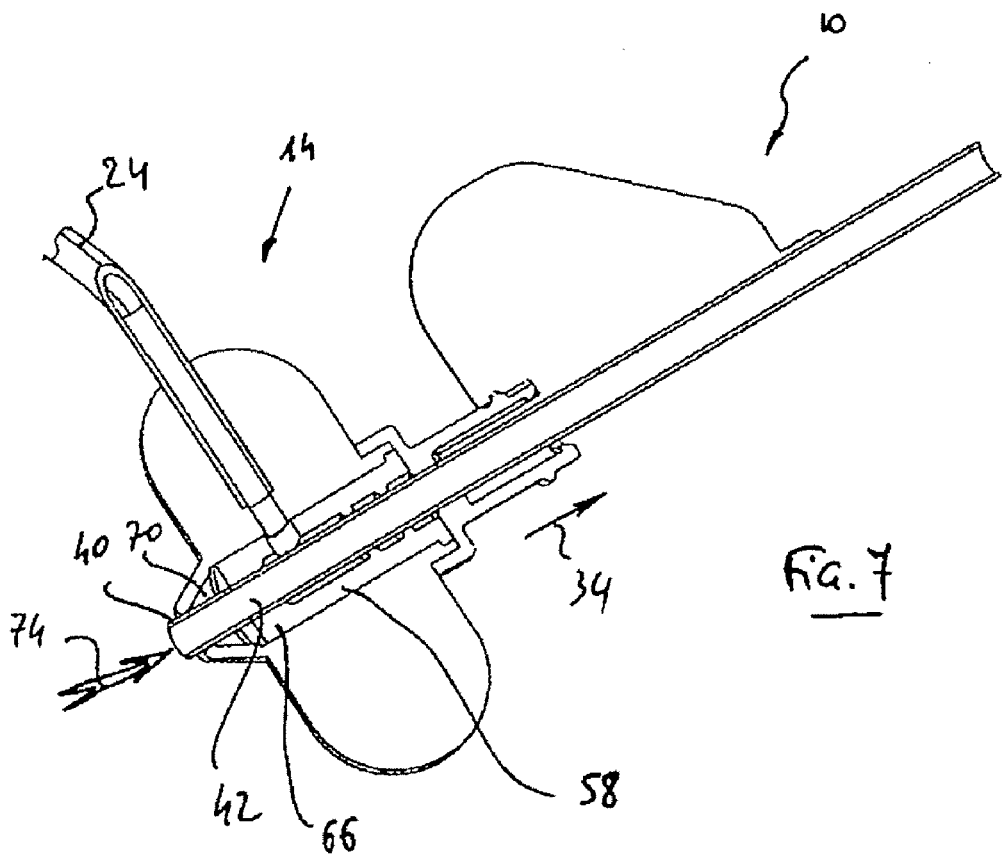

TOOLKIT FOR IMPLANTING AN INTRACORPOREAL LEAD SUCH AS FOR CARDIAC PACING OR SENSING

FIELD OF THE INVENTION

The present invention is directed to the implantation of intracorporal leads, such as leads for cardiac sensing/pacing that are usually associated with "active implantable medical devices" as such devices are defined by the Jun. 20, 1990 directive of the Counsel of European Communities, and more specifically to intracorporal leads for implantable devices for heart pacing, resynchronization, cardioversion and/or defibrillation.

BACKGROUND OF THE INVENTION

Cardiac leads may be endocardial leads, such as leads for sensing/pacing in right heart cavities, or leads introduced in the coronary network, notably leads comprising an electrode positioned in front of a left cavity of the myocardium.

The insertion of the latter type of leads, carried out through endocavitary approaches, is a particularly tricky intervention, taking into account the difficult access to the coronary sinus entrance via the right atrium, and also the required accuracy for the pacing sites once the lead is guided to its desired location and immobilized within the coronary network.

One of the implantation techniques of such a lead requires an accessory known as "guide-catheter". This accessory comprises a hollow tubular sheath reinforced by a wire mesh and with an inner surface presenting a low coefficient of friction (for example, a surface made with PTFE, extruded or co-molded with the rest of the sheath). In addition, the sheath is designed to present a flexibility allowing a stiffness in torsion high enough to allow transmission of a rotational movement applied at one end to the other end, so as to allow guiding the lead tip within the myocardium during the procedure.

Once in place, the guide-catheter serves as a direct "tunnel" between the "external world" and the coronary sinus, a tunnel that can be utilized by the surgeon for sliding the lead therethrough to its final target site.

Once the lead is in place, the guide-catheter needs to be extracted. The extraction procedure is tricky because the lead must not be displaced, or its position or orientation altered as a result of the extraction.

One other difficulty of this extraction step is due to the presence of the electrical connector, at the proximal end of the lead: the diameter of this connector being greater than that of the internal lumen of the guide-catheter, it prevents the guide-catheter from being withdrawn by being simply slid backwardly along the lead.

The step of extracting the guide-catheter therefore usually requires it to be cut, starting from its proximal end and along a generatrix line by means of a slitting tool, also known as "slitter," for slitting the proximal end of the catheter and reinforcement wire mesh forming the frame of the hollow sheath.

With one hand, the surgeon then pulls the guide-catheter towards him with a continuous gesture, while firmly maintaining the lead and the slitting tool with the other hand, allowing the slitting tool to simultaneously slit the sheath as it is being thus extracted.

It has already been proposed in the prior art, in order to avoid resorting to a sharp cutting tool, to use a non-reinforced sheath that is simply strippable; however, cutting of such a sheath along its whole length leads to a weakness and a lower rigidity of the guide-catheter, with a risk of folding and lower transmission of efforts (forces) during its setting up preparatory to an intervention event. It has also been proposed, notably by European patent EP 1,155,710 and its U.S. counterpart U.S. Pat. No. 6,625,496 (commonly assigned herewith to ELA Medical), to provide the lead with a removable connector, which avoids having to cut the guide-catheter. This method however leads to an increasing number of steps required for setting up and assembling the different elements, and also renders the intervention procedure more complicated.

Therefore slitting/cutting of the guide-catheter is, in practice, the most usual way to proceed.

One additional difficulty of this type of intervention comes from the presence, at the proximal end of the guide-catheter, of a hemostatic valve allowing to obdurate at will the internal lumen emerging from the proximal end, opened, of the guide-catheter.

This valve is usually provided with a lateral way (i.e., a passageway) able to communicate with the inner lumen of the guide-catheter, so as to allow purging the guide-catheter after its setting in place, and also eventually injecting therein an antithrombotic agent or radio contrast medium.

This hemostatic valve must meet several requirements, adding to the difficulties explained above. Firstly, the hemostatic valve must be able to allow the lead to pass through it, in order to make the lead penetrate into the guide-catheter then guide it up to its final position. Secondly, once the lead has been set in place, the valve has to be able to be dissociated from the guide-catheter, notably in order to allow the surgeon to initiate the cutting of the guide-catheter sheath so as to extract the latter.

Various configurations of guide-catheter/hemostatic valve sets have been already proposed in the prior art.

In U.S. Pat. No. 6,159,198 (Gardeski), the valve is a removable valve, fit into a coupling bell or "hub" through a Luer Lock type assembly, the hub being formed at the proximal end of the guide-catheter. Closing of the valve is ensured by a screwing mechanism located in the rear area of the valve and allowing to create at will a passage to the inner lumen in order to allow lead insertion. In order to allow cutting of the guide-catheter at the end of the intervention after removal of the valve, the coupling bell is also divisible (cuttable) following a thinner part formed along a generatrix and continued by a transition toward the reinforced sheath.

U.S. published patent application 2005/0,010,238 (Potter) discloses a hemostatic valve mounted at the tip of a guide-catheter on a coupling bell by means of a clipped assembly system. Differently from the Gardeski device, the coupling bell is not divisible (i.e., a bladed tool is required for cutting it), but frangible (i.e. it can be broken into two parts through a force exerted by the fingers of the surgeon, without the need for any additional tool). Once the coupling bell has been thus removed, the proximal end of the guide-catheter is directly accessible, allowing the cutting thereof by means of a usual method using a cutting tool.

U.S. published patent application 2004/0,176,781 (Lindstrom) discloses a toolkit for implanting a lead for a guide-catheter that is not reinforced, but simply strippable, and therefore does not require any cutting tool for its extraction. However, the procedure is rendered more complicated due to the need for resorting to an additional accessory known as TVI or dilator, in order to open the filling element of the valve and protect the lead during the passing through thereof. The dilator also allows increasing the rigidity of the strippable sheath, but of course it also has to be extracted after being used, which requires an additional step in the procedure, the dilator having to also be provided with a strippable structure.

U.S. Pat. No. 6,966,896 (Kurth) describes a toolkit for implanting a lead wherein the valve itself, instead of the coupling bell, is frangible. This allows separating the valve in two parts—the valve initially forming a single block with the guide-catheter—in order to let the proximal tip of the guide-catheter appear, and allow its cutting and extraction.

U.S. published patent application 2007/0123825 describes a toolkit implementing an introducer provided with a valve which can be dissociated in two halves, which are then able to be separated in order to allow peeling the introducer (which can therefore be extracted without the need for a cutting tool). The valve further comprises a means allowing, through pinching the two winglets of the valve, to open, level with the proximal end, an axial hole giving access to the lumen of an axial tubular part that is continuing the introducer. The catheter, provided with the lead, can then be inserted into this hole of the introducer.

All the various devices that have been proposed so far, however, suffer from several difficulties, particularly among them are the following:

- there is always an existing significant risk, during the intervention, of a lead displacement at the moment when the valve is removed and the guide-catheter extracted, especially with those leads that are provided with an electrical connector having a large diameter, as all the accessories that are part of the introducing toolkit have to be removed over this connector;
- the valves that are driven by a screw system require that the surgeon has a very accurate dexterity in order to prevent from damaging the lead by squeezing it too much and, reversely, from creating a lack of tightness during the intervention, due to an insufficient squeezing;
- in the case of a divisible coupling bell, cutting thereof by means of a standard slitter is difficult, due to the brutal variation of the cutting force during the transition between the material of the bell and the reinforced sheath, with a risk of displacing the lead if the forces exerted by the surgeon are not well accurately balanced;
- due to their simplicity, the frangible systems allow an easy removal of the valve, but have the drawback of not comprising any practical mechanism for driving the valve, thus oblige resorting to a dilator for introducing the lead in the valve; this accessory is "floating around" along the lead conductor during the intervention, and anyhow will have to be removed by means of peeling at the end of the intervention;
- the frangible valves that are made as a single block with the guide-catheter, do not allow the surgeon to turn the lateral way around the guide-catheter;
- all the solutions proposed up to now require a certain number of accessories or separate elements, which renders the surgeon's operation more complicated, during the critical step of the guide-catheter extraction, when the surgeon has to be focused on maintaining the position of the lead;
- as the lead has to pass through all these accessories, notably the dilator, the lead electrodes may become polluted, especially by the lubricant usually utilized with the valve.

OBJECTS AND SUMMARY OF THE INVENTION

It is therefore an object of the present invention to palliate one or more of the aforementioned difficulties, by proposing a toolkit comprising a hemostatic valve and a combined guide-catheter, which in combination present one or more of the following advantages:

- a hemostatic valve of the frangible type, reducing the risk of contacting the lead and displacing it during the removal of the valve at the end of the intervention;
- after removal of the valve, obtaining a guide-catheter having a tip free from any element along the cutting direction of the cutting tool, which can in turn be handled with a constant effort (force) during the entire guide-catheter extraction step;
- a simple and effective driving (opening and closing) of the valve, for example, through a simple translation movement, without resorting to any dilator or other type of insertion tool, in order to notably allow direct and free introduction of the lead in the lumen of the guide-catheter;
- direct insertion of the lead in the guide-catheter, without contacting any other element, thus minimizing any risk of polluting the lead during its introduction and passing through the valve;
- obviating any need for an accessory (other than the cutting tool), neither for introducing the lead in the guide-catheter, nor for the removal of the valve and extraction of the guide-catheter;
- providing a valve to freely turn around the guide-catheter, so as to allow orienting the lateral way along any radial direction relating to the guide-catheter hold in position;
- "On-Off"-type driving of the valve between opened and closed positions, with no risk for a leak nor damaging the lead, in contrast to known existing systems such as screwing systems or other mechanisms requiring an accurate dexterity.

Broadly, the present invention is for a toolkit of the general type as described in US 2007/0123825 cited above. One aspect of the invention is directed to a toolkit for setting in place an intracorporal lead, including:

a guide-catheter, having a sheath with an internal lumen opened at its respective distal and proximal ends, and a generatrix, said sheath being able to be opened along the generatrix so as to allow removal of the guide-catheter after use thereof;

a hemostatic valve able to selectively fill the internal lumen of the guide-catheter at the input end, said valve comprising an element that is mobile relative to the guide-catheter between an opened position, where the proximal end of the guide-catheter freely emerges out of the valve to provide an access to the internal lumen of the guide-catheter, and a closed position, where said proximal end of the guide-catheter is filled in a tight manner, wherein the valve is frangible, separating into at least two parts that are dissociable from each other along a median axial plane, wherein:

the sheath comprises a rigidified reinforced sheath, adapted for being cut along said generatrix by means of a cutting tool having a blade;

the guide-catheter presents a constant diameter in its region receiving the valve;

the frangible valve is mounted at the proximal end of the guide-catheter, the proximal end being fitted between said at least two parts of the frangible valve; and said at least two parts of the frangible valve are further each dissociable from the guide-catheter, so as to be able to be separated and moved away from each other to provide free access to the guide-catheter.

Further advantageous characteristics of the present invention include the following. The guide-catheter is essentially devoid of a bell for coupling with its proximal end. The valve comprises a mobile body sliding on the guide-catheter between said extreme opened and closed positions. Preferably, the valve body has a central inner cavity able to receive the proximal end of the guide-catheter, and also has at the distal side of said inner cavity, a material that provides a circumferential tight coupling to the sheath of the guide-catheter.

In yet another embodiment, the valve body has, at the proximal side of the inner cavity, a closure deformable between a first non-stressed position where said closure fills said inner cavity at the proximal side, and a second distended position where the closure is penetrable to be crossed by the sheath of the guide-catheter while ensuring a circumferential tightness with the sheath. The non-stressed position corresponds to said closed position, and the distended position corresponds to said opened position. Further, the valve body preferably embeds an internal part made of an elastically deformable material, said internal part including said circumferential tight coupling at its distal side, and said deformable closure at its proximal side.

The valve preferably comprises a lateral way communicating with a radial derivation of the internal cavity, and is freely mobile in axial rotation around the guide-catheter. In addition, the valve preferably comprises at least one prehension winglet spreading in an axial plane. Similarly, the guide-catheter preferably comprises at least one prehension winglet spreading in an axial plane.

In one preferred embodiment, the valve comprises means for locking said valve in at least one position selected from among an opened and a closed position. Such a locking means can include cooperating fitting means respectively provided on the valve body and on an axial extension of the guide-catheter

BRIEF DESCRIPTION OF THE DRAWINGS

Further features, advantages and characteristics of the present invention will become apparent to a person of ordinary skill in the art in view of the following detailed description of preferred embodiments of the invention, made with reference to the drawings annexed in which like reference characters refer to like elements, and in which:

FIG. 4 is a section view in an axial plane, showing the details of the internal structure of the hemostatic valve in its closed position, and showing the way the tightness is ensured at different levels of this valve;

FIG. 5 is a partial view, in section in an axial plane, showing the stop mechanisms of the valve in a closed position, and locking mechanisms of the valve on the guide-catheter in an opened position; and FIGS. 6 and 7 are schematics, in section in an axial plane, respectively showing the way the different elements of the guide-catheter and the valve communicate with each other, in the closed and opened positions of the valve.

DETAILED DESCRIPTION OF THE INVENTION

Figure 1:
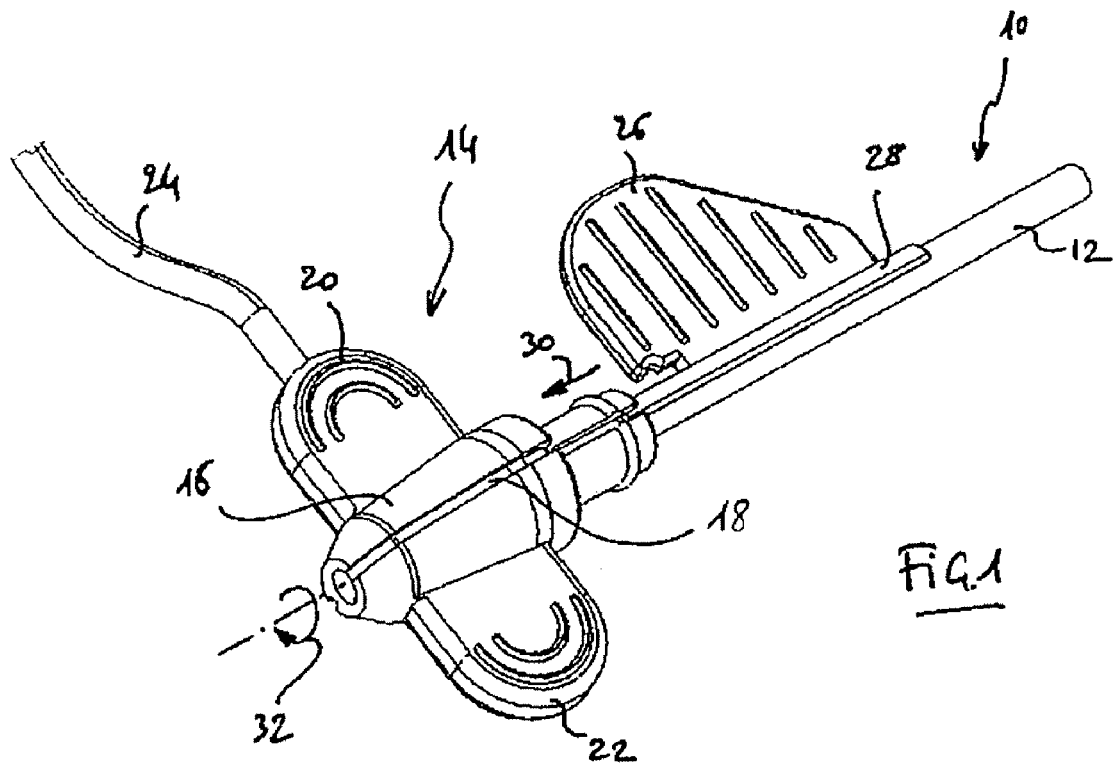
FIG. 1 is a perspective view of the guide-catheter/hemostatic valve set, according to a preferred embodiment of the present invention, in the closed position.
Figure 2:
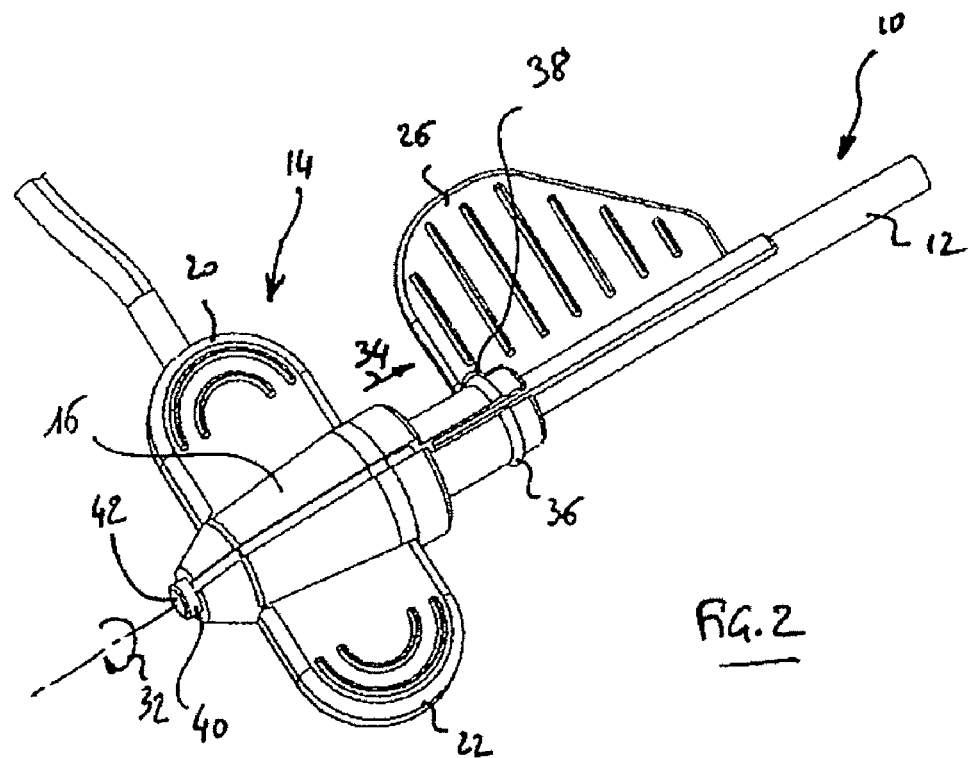
FIG. 2 is a perspective view of the guide-catheter/hemostatic valve set of FIG. 1, in the opened position.
Figure 3:
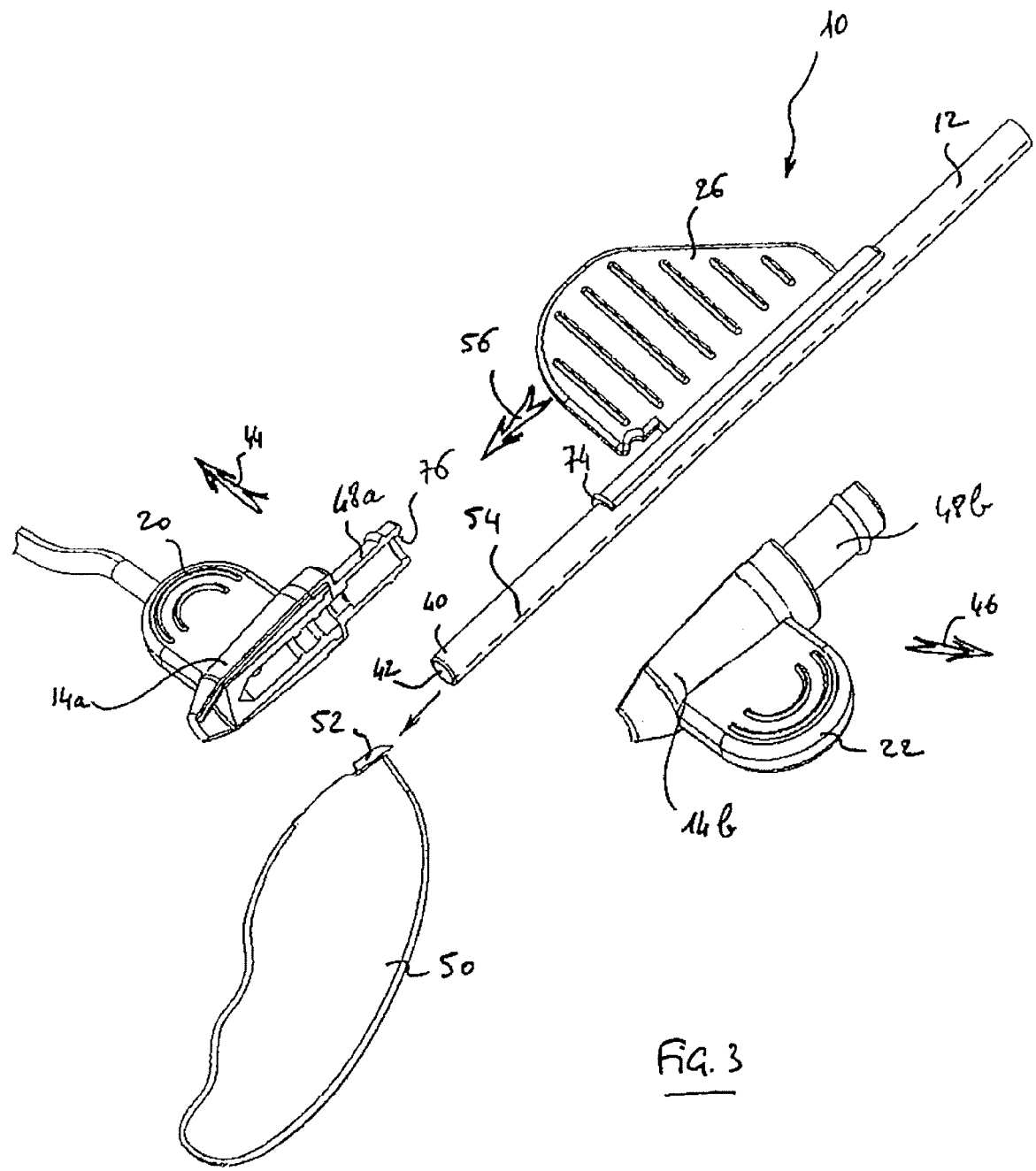
FIG. 3 shows the step of removal of the hemostatic valve after breaking thereof, and placing the cutting tool facing the guide-catheter so as to allow slitting the sheath and extraction of the guide-catheter.

One will now describe an example embodiment of a toolkit in accordance with the present invention. With reference to the drawings, FIGS. 1 to 7 show the different aspects of an exemplary set comprising a guide-catheter and associated hemostatic valve, the valve being represented either in "closed" position (FIGS. 1 and 7) or "open" position (FIGS. 2, 4, 5 and 6), or after separating the valve from the guide-catheter, right after cutting thereof (FIG. 3).

The guide-catheter 10 comprises a hollow sheath 12 reinforced with a wire mesh in order to improve its rigidity; once the guide-catheter is in place, its proximal end (the one that is visible on the figures) is emerging from the introduction site, the surgeon using this emerging part for introducing, driving and positioning the lead at its final target site.

The proximal end of the guide-catheter 10 is provided with a hemostatic valve 14 allowing to selectively fill the internal lumen of sheath 12 at its input end.

In a characteristic manner of this invention, valve 14 comprises a mobile body 16 sliding on the guide-catheter 10 between two extreme positions defining the "opened" and "closed" states of the valve, the valve being driven between these two states through a very simple movement of the "push-pull" type.

The body 16 of the valve 14 comprises all along its length, along two diametrically opposite generatrices, an area with a thinner thickness 18, forming a fracture initiation score and thus rendering the valve frangible, i.e., able to be broken apart in two dissociable parts at both sides around a median plane comprising the fracture initiation scores 18.

In order to facilitate its driving, the valve is provided with two opposite lateral winglets 20, 22 spreading in the illustrated embodiment in an axial plane. These winglets also allow, as it will be described below, to exert on the valve an effort sufficient for breaking it into two parts, when it comes time to remove it at the end of the intervention. It should be understood that the winglets need not be in a common plane.

In addition, in a manner that is already known per se, the valve is provided with a lateral way 24 able to come and communicate with the internal lumen of the guide-catheter so as to allow its purge, and eventually injecting a radio contrast medium or an antithrombotic agent.

In order to facilitate its handling, the guide-catheter 10 is also provided with a prehension winglet 26 preferably spreading in an axial plane, and for instance constituting the continuation of a longitudinal reinforcement 28, integral of sheath 12 and spreading circumferentially on a part thereof (so as to allow ulterior cutting without any interference from element 28).

It is easy for the surgeon to drive the valve by holding the winglet 26 of the guide-catheter in one hand, and in the other hand one of the winglets 20 or 22 of the valve, for example by moving these winglets away from each other (arrow 30) to put the valve in its "closed" position. It shall be further noticed that the valve is freely mobile in rotation around the guide-catheter 10 (arrow 32), which allows orienting the lateral way 24 along any possible direction providing as little as possible constraint for the surgeon.

With an opposite movement (arrow 34 in FIG. 2), the surgeon will put the valve in its "opened" position by moving the winglets 20, 22 of the valve and winglet 26 of the guide-catheter closer to each other. The valve will be hold in this position by a lock mechanism using a neck 36 formed on the body 16 of the valve in the most distal area thereof, this neck 36 being fitting in a recess 38 formed in the winglet 26 of the guide-catheter.

It should be understood that the valve as implemented in the present invention gives immediate tactile information to the practitioner as to the effective position, opened or closed, of the valve, in contrast to other existing devices such as valves with a screw element. It is further possible to add a visual marking appropriate for rendering this indication on the valve's position even more apparent.

It should be understood by a person of ordinary skill in the art that, in the opened position of the valve, the emerging end 40 of sheath 12 of the guide-catheter 10 emerges from the most proximal part of body 16 of the valve, thus giving access to the internal lumen 42 of the guide-catheter (see FIG. 2), in order to preferably allow introducing the lead in this lumen.

After placing the lead at its final position, it is required to extract the guide-catheter, no longer utilized, by taking all required precautions so as not to displace the lead during the extraction procedure.

The first step consists of removing the valve to allow direct access to the end of the catheter.

As disclosed above, valve 14 is a frangible valve, which can be broken in two parts 14a, 14b that are roughly symmetrical (see FIG. 3) around an axial median plane, through a bending stress exerted by the surgeon on the two opposite winglets 20, 22. The two halves 14a, 14b can then be separated and moved away from each other (arrows 44, 46). This grants access to the guide-catheter, no longer fitted between the two halves 48a, 48b of the valve body.

The guide-catheter can then be cut, in a manner already known per se, by means of a cutting tool or "slitter" 50 comprising a blade 52 allowing to slit the reinforced sheath of the guide-catheter. The tool 50 is immobilized by a surgeon's hand, and with his/her other hand, the surgeon pulls the guide-catheter toward him/her, preferably with help from winglet 26, so as to slit the sheath 12 along a generatrix 54. This movement of cutting and extracting the guide-catheter is pursued until complete extraction thereof (arrow 56).

FIGS. 4 to 7 are section views showing the internal configuration of the elements of valve 14, mounted on the guide-catheter 10. The valve body embeds an internal part 58 that is made of a material that is elastically deformable, for example, a silicone material co-assembled or co-molded with the valve body, which is itself made of a relatively rigid material such as polypropylene or polyamide.

In its distal area 60, the elastic part 58 defines a central cavity 62 of cylindrical shape, in which the sheath 12 of guide-catheter 10 penetrates. The tightness between the elastic part 58 and sheath 12 is ensured by one or more internal circumferential reliefs 64 filling the cavity 62, and thus the internal lumen 42 of the guide-catheter, in a tight manner vis-à-vis the external environment.

At its proximal end 66, the elastic part 58 is closed, i.e., the cavity 62 is a one-eyed cavity only opened toward its distal direction. The wall closing the elastic part 58 however is a penetrable closure, thanks to a piercing or a slot 68. In the free or non-stressed position, thanks to the elasticity of the material of part 58, this closure closes the cavity 62 in a tight manner, but it can be penetrated and crossed through an external stress such as by an axially driven element, that is, in the present case, the tip 40 of the sheath of the guide-catheter 10 which crosses the closure when the valve is moved (arrow 34) to the "opened" position. As shown in FIG. 7, the closure is then dilated and crossed by the tip 40 of the guide-catheter, which freely emerges from the valve through a hole 70 formed in the proximal area of the valve body.

Also, the internal cavity 62 is provided with a radial hole 72 allowing to make this cavity 62, and therefore the internal lumen 42 of the guide-catheter 10, communicate with the lateral way 24 of the valve.

With reference to FIG. 5, further details of the stop and locking mechanism of the valve on the guide-catheter are shown.

Firstly, when the valve is moved toward its closed position (arrow 30), a skirt 74, formed at the end of reinforcement part 28 integral of the guide-catheter, bumps against a neck 76 formed at the distal tip of the valve body. In addition to acting as a stop, allowing to geometrically define the "closed" position of the valve, these cooperating elements ensure the mutual integration of the guide-catheter and the valve, while allowing a degree of freedom in axial rotation of the valve around the guide-catheter, as explained above. The guide-catheter can only be separated from the valve by breaking the valve, as described above in reference to FIG. 3, the skirt 74 of the guide-catheter being thereafter simply retained by the neck 76 of the valve.

FIG. 5 also shows the elements allowing to define the "open" position of the valve and locking in that position, thanks to a neck 36 of the valve fitting in a recess 38 of the winglet 26 integral with the guide-catheter.

FIGS. 4 and 6 show the respective "closed" and "opened" positions of the guide-catheter and the valve, respectively. As explained above, switching from one position to the other is achieved simply by a "push-pull" driving of the valve relative to the guide-catheter (arrows 30, 34). This driving is of the "On-Off" type and does not require any specific handling or balancing of efforts (driving forces), in contrast to the known screwing mechanisms used in the prior art.

The easy and fast driving of the valve between the two positions further dramatically reduces the risks of air ingress (and embolism) or blood leak during the intervention, therefore enhances the safety of setting up the lead.

It should be understood that in opened position (see FIG. 7), the proximal end 40 of the guide-catheter freely emerges from the valve body, which allows to directly insert the lead in the guide-catheter, with no risk of polluting the lead, for the guide-catheter itself acts as a dilator for opening the closure 68 of the valve. This further prevents from resorting to any specific tool, thus eliminates all the drawbacks listed associated therewith referenced above.

It also should be understood that the emergence of the guide-catheter at the proximal end of the valve provides a visual indication, simple and unambiguous, of the opened position of the valve.

One skilled in the art will appreciate that the present invention can be practiced by other than the described embodiments which are presented for purposes of illustration and not of limitation.

I claim:

1. A toolkit for setting in place an intracorporal lead, comprising:
    a guide-catheter, having a sheath including a distal end, a proximal end, and an internal lumen opened at the distal and proximal ends, and a generatrix, said sheath being able to be opened along the generatrix so as to allow removal of the guide-catheter after use thereof;
    a hemostatic valve able to selectively fill the internal lumen of the guide-catheter at the input end, said valve comprising an element mobile longitudinally slidable along the guide-catheter between an opened position where the proximal end of the guide-catheter freely emerges out of the valve to provide an access to the internal lumen of the guide-catheter, and a closed position where said proximal end of the guide-catheter is filled in a tight manner, said valve being frangible into at least two parts dissociable from each other along a median axial plane, wherein:
    the sheath comprises a rigidified reinforced sheath, adapted for being cut along said generatrix by means of a cutting tool comprising a blade;

the guide-catheter presents a constant diameter in its region receiving the valve;

the frangible valve is mounted at the proximal end of the guide-catheter, and is fitted between said at least two parts of the frangible valve; and the dissociation of said at least two parts of the frangible valve provide free access to the guide-catheter.

2. The toolkit of claim 1, wherein the guide-catheter is essentially devoid of a bell for coupling with its proximal end.

3. The toolkit of claim 1, wherein the valve further comprises a central inner cavity able to receive the proximal end of the guide-catheter, and, at the distal side of said inner cavity, a material providing a circumferential tightness with the sheath of the guide-catheter.

4. The toolkit of claim 3, wherein the valve further comprises, at the proximal side of the inner cavity, a closure deformable between a first non-stressed position, where said closure fills said inner cavity at the proximal side, and a second distended position, where the closure is crossable by the sheath of the guide-catheter while ensuring a circumferential tightness with the sheath, the non-stressed position corresponding to said closed position, and the distended position corresponding to said opened position.

5. The toolkit of claim 4, wherein the valve further comprises an internal part embedded therein, said internal part being made of an elastically deformable material, said internal part including said material providing circumferential tightness at its distal side, and said deformable closure at its proximal side.

6. The toolkit of claim 3, wherein the valve further comprises a lateral way communicating with a radial derivation of the internal cavity.

7. The toolkit of claim 1, wherein the valve is freely mobile in axial rotation around the guide-catheter.

8. The toolkit of claim 1, wherein the valve comprises at least one prehension winglet spreading in an axial plane.

9. The toolkit of claim 1, wherein the guide-catheter further comprises at least one prehension winglet spreading in an axial plane.

10. The toolkit of claim 1, wherein the valve further comprises means for locking said valve in at least one position selected from among an opened position and a closed position.

11. The toolkit of claim 10, wherein said locking means further comprises a cooperating fittings respectively provided on the valve body and on an axial extension of the guide-catheter.

* * * * *